(12) United States Patent
Rayfield et al.

(10) Patent No.: US 11,389,334 B2
(45) Date of Patent: Jul. 19, 2022

(54) APPARATUS FOR APPLYING A COMPRESSION BANDAGE

(71) Applicants: Tanya Rayfield, Helotes, TX (US); John Rayfield, Helotes, TX (US)

(72) Inventors: Tanya Rayfield, Helotes, TX (US); John Rayfield, Helotes, TX (US)

( * ) Notice: Subject to any disclaimer, the term of this patent is extended or adjusted under 35 U.S.C. 154(b) by 364 days.

(21) Appl. No.: 16/576,761

(22) Filed: Sep. 19, 2019

(65) Prior Publication Data
US 2020/0085631 A1    Mar. 19, 2020

Related U.S. Application Data

(60) Provisional application No. 62/733,597, filed on Sep. 19, 2018.

(51) Int. Cl.
*A61F 13/00* (2006.01)
*A61F 13/06* (2006.01)
*A61F 2/78* (2006.01)

(52) U.S. Cl.
CPC ...... *A61F 13/00085* (2013.01); *A61F 2/7812* (2013.01); *A61F 13/06* (2013.01); *A61F 2002/7825* (2013.01); *A61F 2002/7875* (2013.01); *A61F 2013/0028* (2013.01)

(58) Field of Classification Search
CPC .... A61F 15/005; A61F 13/0085; A61F 13/06; A61F 13/08; A61F 2/7812; A61F 2002/7825; A61F 2002/7818; A61F 2002/7875; A47G 25/90; A47G 25/905; A47G 25/9073; A47G 25/907

USPC ........................................ 602/901
See application file for complete search history.

(56) References Cited

U.S. PATENT DOCUMENTS

| | | | | |
|---|---|---|---|---|
| 1,992,344 A | * | 2/1935 | Alhadate | A61F 15/005 602/63 |
| 2,571,946 A | * | 10/1951 | Rosenfield | A61F 13/105 602/1 |
| 2,739,587 A | * | 3/1956 | Scholl | A61F 15/005 602/1 |
| 3,358,682 A | * | 12/1967 | Norman | A61F 15/005 602/1 |
| 3,941,125 A | * | 3/1976 | Drake | A61F 15/005 206/441 |
| 6,869,410 B1 | * | 3/2005 | Mosemiller | A61F 15/005 128/878 |
| 9,635,967 B1 | * | 5/2017 | Hopper | A47G 25/90 |
| 10,568,769 B2 | * | 2/2020 | Hutchful | A61F 13/00017 |
| 2009/0120975 A1 | * | 5/2009 | Schoepe | A47G 25/905 223/111 |

(Continued)

FOREIGN PATENT DOCUMENTS

| | | | | |
|---|---|---|---|---|
| CA | 2272661 A1 | * | 11/2000 | ........... A47G 25/905 |
| DE | 4228916 A1 | * | 3/1994 | ........... A47G 25/905 |

(Continued)

*Primary Examiner* — Kim M Lewis
(74) *Attorney, Agent, or Firm* — Shah IP Law, PLLC

(57) ABSTRACT

An apparatus for applying a compressive bandage on a residual limb enables a user to apply a compression bandage to his or her residual limb without assistance from a physical therapist or an assistant. As used herein, the compressive bandage serves as a transition layer between a residual limb and a prosthetic device. The apparatus enables a user to apply a compression bandage by simply moving his or her residual limb through the device.

10 Claims, 6 Drawing Sheets

(56) References Cited

U.S. PATENT DOCUMENTS

2010/0147908 A1\* 6/2010 Skerman .............. A47G 25/905
                                                                        223/111
2014/0039362 A1\* 2/2014 McVeigh .............. A61F 15/005
                                                                        601/134

FOREIGN PATENT DOCUMENTS

| | | | | | |
|---|---|---|---|---|---|
| GB | 858821 A | \* | 1/1961 | ........... | A61F 15/005 |
| GB | 2211740 A | \* | 7/1989 | ........... | A61F 15/005 |

\* cited by examiner

APPARATUS FOR APPLYING A COMPRESSION BANDAGE

CROSS-REFERENCE TO RELATED APPLICATIONS

This application claims priority to U.S. Provisional Patent Application Ser. No. 62/733,597, filed Sep. 19, 2018, entitled "Apparatus for applying a compression bandage." The entire content of that application is incorporated herein by reference.

BACKGROUND

Field of the Art

This disclosure relates to medical devices. Specifically, this disclosure relates to applying compressive bandages to injured and/or amputated limbs.

Discussion of the State of the Art

Compression bandages—more commonly known as (and herein also referred to as) stump shrinkers—are typically applied over injured limbs to reduce, prevent, or control swelling (edema) of the limb. Stump shrinkers are most commonly applied after surgery. But, they are also applied over a limb whenever a user wishes to use a prosthetic limb. When used in such a manner, the stump shrinker serves an intermediate layer between a residual limb and a prosthetic.

Stump shrinkers typically look like compression socks and are notoriously difficult to wear. Patients who have undergone an amputation typically have limited mobility and range, and thus, find it difficult to apply a stump shrinker. For example, a patient who has lost an arm may find it very difficult to apply a stump shrinker with only one available arm. Moreover, amputees who have recently undergone surgery, or have experienced loss of strength, often do not have requisite strength of pull a stump shrinker over a residual limb. Some even find it painful to apply a compression bandage because of the difficulties involved. These patients are therefore extremely frustrated with the process of applying a stump shrinker.

Amputees, therefore, typically have to rely on others to help them with compression bandages, or, if assistance is not available, they often have to make the difficult choice of foregoing bandages altogether, which may cause medical complications. Currently, there are no assistive apparatuses for helping patients apply stump shrinkers independently, with ease, and in an effective manner.

SUMMARY

The present invention overcomes many of the issues described above by providing an applicator apparatus for applying a compressive bandage around a user's residual limb. Specifically, the present invention may insert his or her residual limb within an opening within the apparatus to apply the apparatus.

A feature of the present invention is that it is capable of single user operation. As such, the present invention permits an individual with an amputated limb to apply a compression bandage by himself or herself without assistance from someone else. This is a significant improvement over the prior art, which typically requires assistance from a physical therapist or an assistance. By permitting single user operation, the inventive apparatus significantly improves the quality of life of the amputee. In one embodiment of the invention, the apparatus is comprised of an assistance mechanism that permits a user use the apparatus to apply a compressive bandage on himself or herself. The assistance mechanism may be comprised of a handle that may be disposed on the exterior of the device. However, the design of the device itself enables self-administration without assistance from others.

Another feature of the present invention is that it permits pain-free application of the compressive bandage around a residual limb. The prior art method of application causes significant discomfort and pain to the amputee because it is difficult to apply a compressive bandage to an amputated limb, especially while it is healing or if the user is trying to fit a new prosthetic. The present invention enables a user to apply a compressive bandage without requiring significant additional readjustment or painful applicators.

In accordance with an embodiment of the invention, the present invention is for an apparatus for applying a compressive bandage on a residual limb that has been amputated, the apparatus comprising a housing having an interior portion, an exterior portion, an entrance portion, and an exit portion, the interior portion defining an opening that is accessible from the entrance portion and the exit portion, the opening being large enough to accommodate a residual limb, an attachment mechanism for attaching a compressive bandage to the housing, the attachment mechanism enabling an attached compressive bandage to extend across the interior portion of the housing, and a release mechanism for releasing the attached compressive bandage from the attachment mechanism, the release mechanism configured to release the attached compressive bandage once the garment has sufficiently enveloped a residual limb that may be travelling through the opening defined by the interior portion.

In one embodiment, the apparatus may be further comprised of an adjustment mechanism for expanding and/or contracting the diameter of the opening. In one embodiment, the adjustment mechanism may expand and/or contract the diameter of the entrance portion. In another embodiment, adjustment mechanism may expand and/or contract the diameter of the exit portion. In one embodiment, the adjustment mechanism is comprised of a ratcheting system that may be manipulated with a handle. The ratcheting system may be manipulated to increase and/or decrease the diameter of the of the opening of the apparatus.

In one embodiment, the interior portion of the apparatus is tapered such that the diameter of the entrance portion is greater than the diameter of the exit portion. In one embodiment, the interior portion is tapered such that the diameter of the exit portion is greater than the diameter of the entrance portion.

In one embodiment, the apparatus is further comprised of an assistance mechanism to assist a user in passing a residual limb through the opening. The assistance mechanism may be comprised of a handle that may be pulled and/or pushed to help a user pass a residual limb through the opening. In other embodiment, the assistance mechanism may be comprised of a ring that a user can slide his or her finger or hand through. Other assistance mechanisms that may be used to pull the apparatus towards the user and/or push the apparatus away from the user may be used without departing from the scope of invention. In one embodiment, the assistance mechanism may be disposed on the exterior portion of the apparatus. In one embodiments, the assistance mechanism may be disposed on the entrance portion and/or the exit portion of the apparatus.

BRIEF DESCRIPTION OF THE DRAWING FIGURES

The accompanying drawings illustrate several embodiments and, together with the description, serve to explain the principles of the invention according to the embodiments. It will be appreciated by one skilled in the art that the particular arrangements illustrated in the drawings are merely exemplary and are not to be considered as limiting of the scope of the invention or the claims herein in any way.

DETAILED DESCRIPTION

Figure 1:
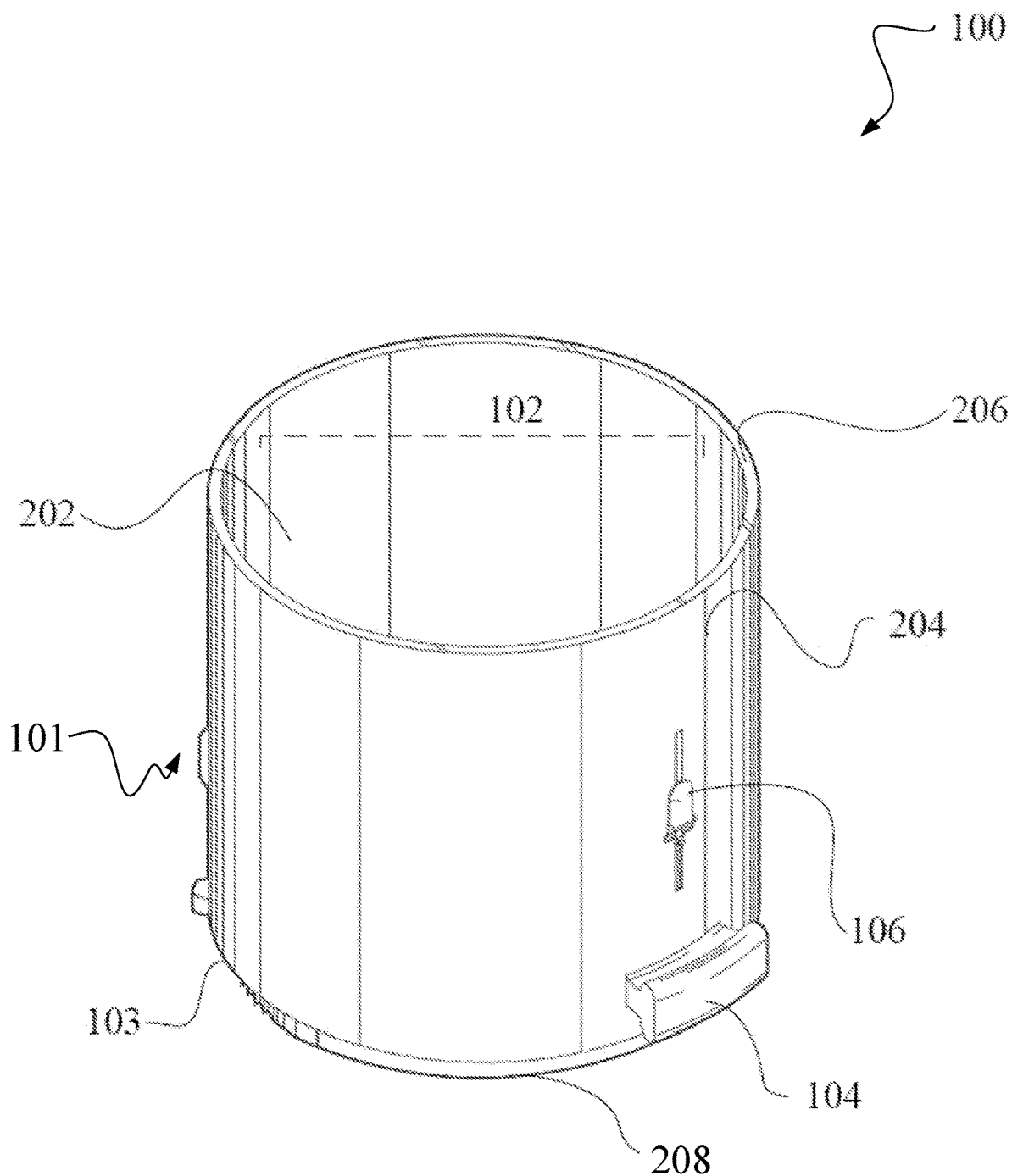
FIG. 1 illustrates an exemplary embodiment of the inventive apparatus from a top perspective view.

In accordance with an embodiment of the invention, the present invention is for an apparatus for applying a compressive bandage on a residual limb that has been amputated, the apparatus comprising a housing having an interior portion, an exterior portion, an entrance portion, and an exit portion, the interior portion defining an opening that is accessible from the entrance portion and the exit portion, the opening being large enough to accommodate a residual limb, an attachment mechanism for attaching a compressive bandage to the housing, the attachment mechanism enabling an attached compressive bandage to extend across the interior portion of the housing, and a release mechanism for releasing the attached compressive bandage from the attachment mechanism, the release mechanism configured to release the attached compressive bandage once the garment has sufficiently enveloped a residual limb that may be travelling through the opening defined by the interior portion.

The invention is described by reference to various elements herein. It should be noted, however, that although the various elements of the inventive apparatus are described separately below, the elements need not necessarily be separate. The various embodiment may be interconnected and may be cut out of a singular block or mold. The variety of different ways of forming an inventive apparatus, in accordance with the disclosure herein, may be varied without departing from the scope of the invention.

Generally, one or more different embodiments may be described in the present application. Further, for one or more of the embodiments described herein, numerous alternative arrangements may be described; it should be appreciated that these are presented for illustrative purposes only and are not limiting of the embodiments contained herein or the claims presented herein in any way. One or more of the arrangements may be widely applicable to numerous embodiments, as may be readily apparent from the disclosure. In general, arrangements are described in sufficient detail to enable those skilled in the art to practice one or more of the embodiments, and it should be appreciated that other arrangements may be utilized and that structural changes may be made without departing from the scope of the embodiments. Particular features of one or more of the embodiments described herein may be described with reference to one or more particular embodiments or figures that form a part of the present disclosure, and in which are shown, by way of illustration, specific arrangements of one or more of the aspects. It should be appreciated, however, that such features are not limited to usage in the one or more particular embodiments or figures with reference to which they are described. The present disclosure is neither a literal description of all arrangements of one or more of the embodiments nor a listing of features of one or more of the embodiments that must be present in all arrangements.

Headings of sections provided in this patent application and the title of this patent application are for convenience only and are not to be taken as limiting the disclosure in any way.

Devices and parts that are connected to each other need not be in continuous connection with each other, unless expressly specified otherwise. In addition, devices and parts that are connected with each other may be connected directly or indirectly through one or more connection means or intermediaries.

A description of an aspect with several components in connection with each other does not imply that all such components are required. To the contrary, a variety of optional components may be described to illustrate a wide variety of possible embodiments and in order to more fully illustrate one or more embodiments. Similarly, although process steps, method steps, or the like may be described in a sequential order, such processes and methods may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the embodiments, and does not imply that the illustrated process is preferred. Also, steps are generally described once per aspect, but this does not mean they must occur once, or that they may only occur once each time a process, or method is carried out or executed. Some steps may be omitted in some embodiments or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other embodiments need not include the device itself.

Techniques and mechanisms described or referenced herein will sometimes be described in singular form for clarity. However, it should be appreciated that particular embodiments may include multiple iterations of a technique or multiple instantiations of a mechanism unless noted otherwise. Alternate implementations are included within the scope of various embodiments in which, for example, functions may be executed out of order from that shown or discussed, including substantially concurrently or in reverse order, depending on the functionality involved, as would be understood by those having ordinary skill in the art.

The inventive system and method (hereinafter sometimes referred to more simply as "system" or "method") described herein significantly reduces the time, difficulty, and frustration associated with applying a stump shrinker on a residual limb.

Figure 2:
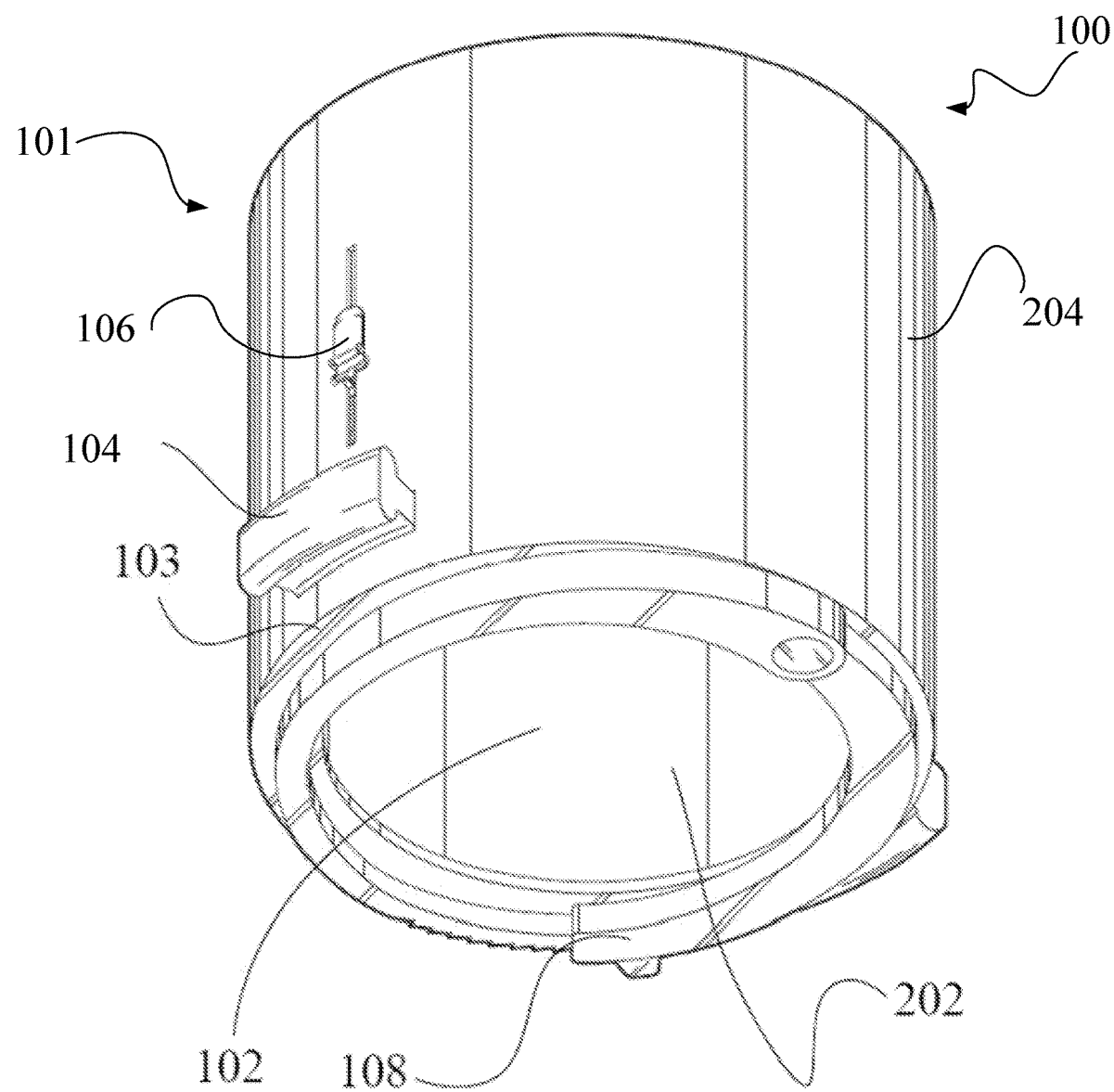
FIG. 2 illustrates an exemplary embodiment of the inventive apparatus from a bottom perspective view.

In accordance with one embodiment of the invention, and as illustrated in FIGS. 1-10, the inventive apparatus may be comprised of a variety of elements. Specifically, as illustrated in FIG. 1 and FIG. 2, the apparatus 100 may be comprised of an housing 101, comprising an interior portion 202, an exterior portion 204, an entrance portion 206, and an exit portion 208, the housing defining an opening 102 within the interior portion 202, an attachment mechanism 103, an assistance mechanism 104, a release mechanism 106, and an adjustment mechanism 108. Some components may be added, removed, or substituted, as described in the specification, and as would be understood by a person of ordinary skill in the art. As noted above, the components described in FIG. 1 and FIG. 2 are for illustration purposes only. Certain components may be added, modified, changed, or removed in accordance with this description, and as would be apparent to a person of ordinary skill in the art without departing from the scope of the invention.

Figure 3:
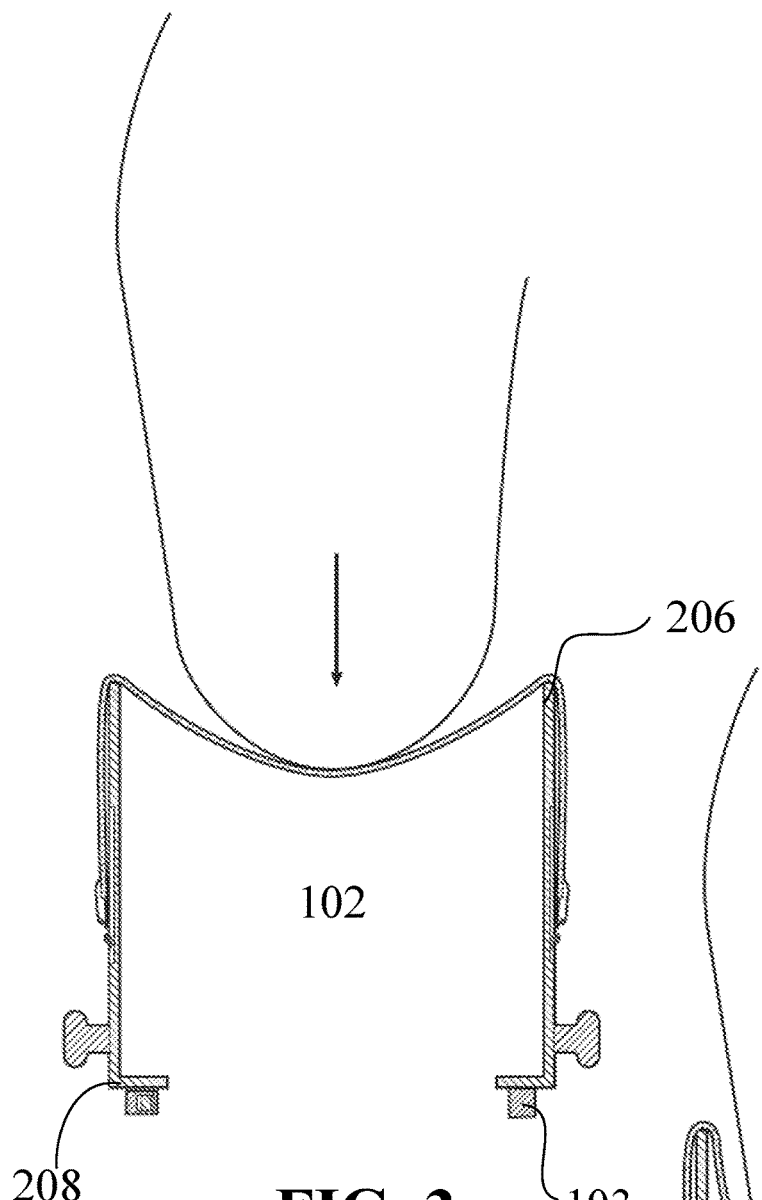
FIG. 3 illustrates, in accordance with an embodiment of the invention, a residual limb travelling through an opening of the inventive apparatus.
Figure 4:
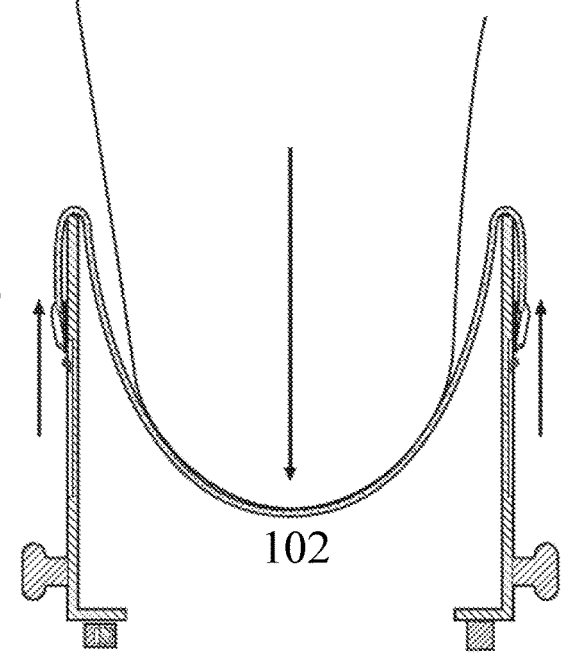
FIG. 4 illustrates, in accordance with an embodiment of the invention, a residual limb travelling through an opening of the inventive apparatus.
Figure 5:
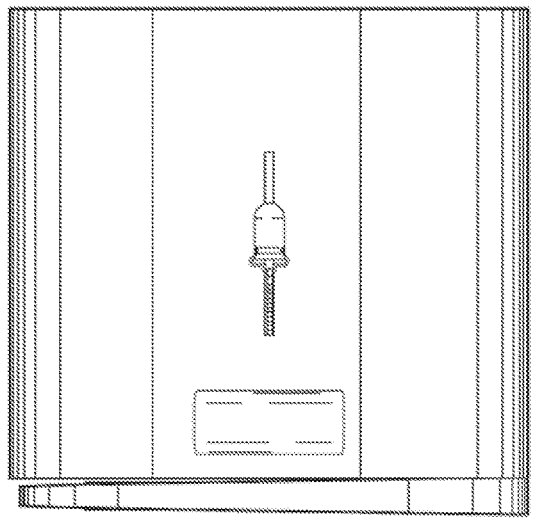
FIG. 5 illustrates an exemplary embodiment of the inventive apparatus from a front view.
Figure 6:
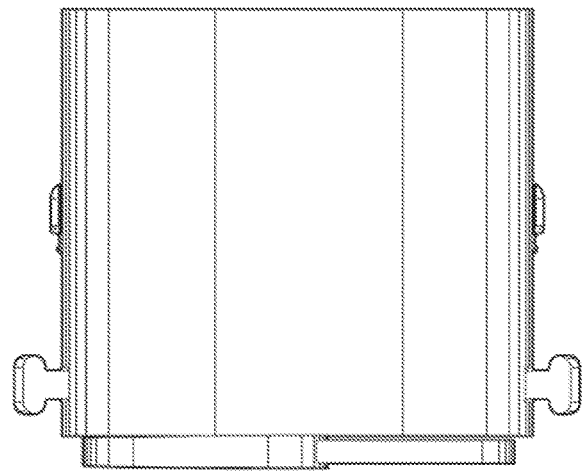
FIG. 6 illustrates an exemplary embodiment of the inventive apparatus from a side view.
Figure 7:
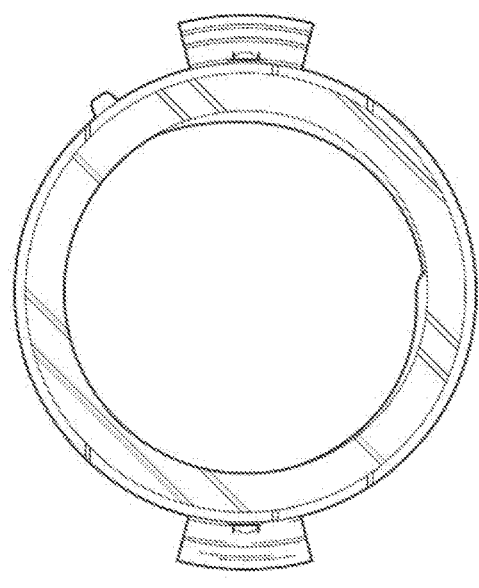
FIG. 7 illustrates an exemplary embodiment of the inventive apparatus from a top view.
Figure 8:
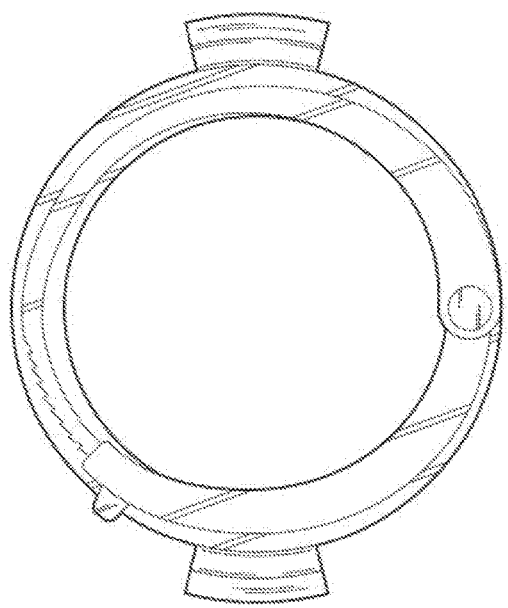
FIG. 8 illustrates an exemplary embodiment of the inventive apparatus from a bottom view.
Figure 9:
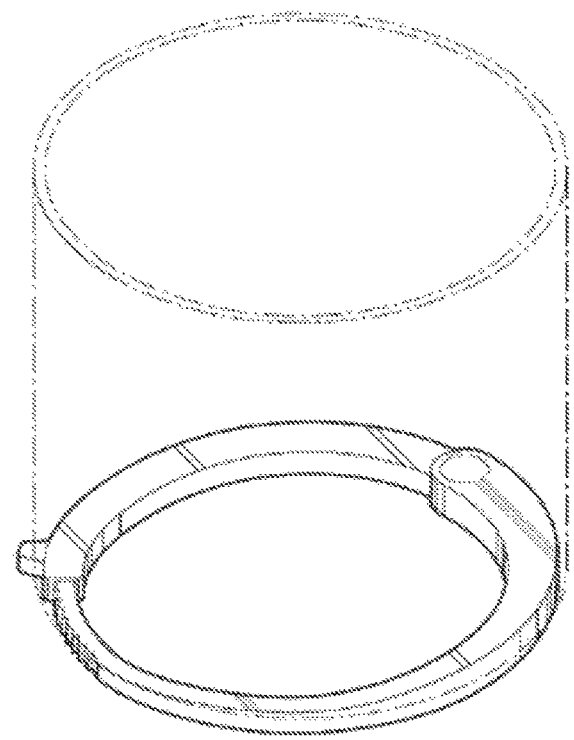
FIG. 9 illustrates an adjustment mechanism in an open configuration, in accordance with an exemplary embodiment of the invention.
Figure 10:
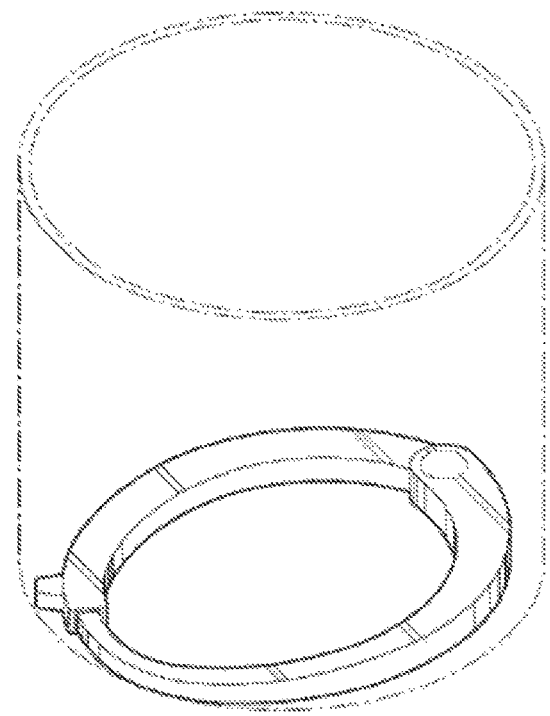
FIG. 10 illustrates an adjustment mechanism in a closed configuration, in accordance with an exemplary embodiment of the invention.

As illustrated in FIGS. 3 and 4, in one exemplary method of use, a user may use the apparatus 100 by moving his or her residual limb through the opening from the entrance portion 206 through the exit portion 208 of the apparatus 100. A compression bandage extending across the entire surface area of the entrance portion 206 would envelope the user's residual limb as it moves through the opening and against the compression bandage. Once sufficiently covered, the user may release the compression bandage from the apparatus to fully apply the bandage to the residual limb. Thereafter, the user may remove the apparatus 100 (which is now without any compression bandage) by simply sliding the apparatus off the user's limb.

The specific components of the apparatus 100, and the methods for applying a compression bandage are discussed in greater detail below.

Now referring to FIGS. 1 and 2, in one exemplary embodiment, the apparatus 100 includes a housing 101. The housing may be comprised of an interior portion 202, an exterior portion 204, an entrance portion 206, and an exit portion 208, the housing defining an opening 102 within the interior portion 202. Although the various figures provided herein disclose a circular or an oval shaped housing 101, a variety of different shapes and sizes may be deployed, as would be readily understood by a person of ordinary skill in the art, without departing from the scope of the invention.

As would be apparent to a person of ordinary skill in the art, the housing 101 may be comprised of a variety of different materials without departing from the scope of the invention including, but not limited to metal, aluminum, steel, tin, etc. In one embodiment, the housing 101 may be washable and reusable.

In one embodiment, the housing 101 is comprised of sufficient strength to resist compression or deformation that may be caused by a user pulling the apparatus towards or away from the user as the user applies force against a compressive bandage.

The interior portion 202 of the housing 101 defines an opening 102 that is bound by an entrance portion 206 on one side, and an exit portion 208 on the other end. The opening 102 may be an aperture or a cavity, wherein a user may extend his or her limb through the opening from the entrance portion 206 to the exit portion 208 (or vice versa). The diameter of the opening 102 may be variable and can be as large or as small as necessary to accommodate various residual limbs.

In one embodiment, the opening 102 may be cylindrical in shape, and may extend the entire length of the apparatus 100. In other embodiments, the opening may be circular or toroidal in shape. In certain embodiments, the opening 102 may also be tapered in shape such that the opening or aperture on one end is larger than the opening or aperture on the other end.

The apparatus 100 includes an attachment mechanism 103 for attaching a compression bandage to the apparatus 100. In one embodiment, the attachment mechanism is next to and parallel to the exit portion 208. In such an embodiment, the compression bandage extends across the diameter that is defined by the attachment mechanism 103.

The attachment mechanism 103 also includes a mechanism for permitting the compression bandage to slide out of the attachment mechanism when sufficient force is applied to the compression bandage that is extending across surface plane defined by the opening (when the force is applied in a direction that is orthogonal to the surface place).

The apparatus 100 also includes a release mechanism 106. The release mechanism 106, when activated by the user, releases the compression bandage that was previously attached to the apparatus 100 via the attachment mechanism 103. For example, once a user activates the release mechanism 106, the compression bandage is released from the apparatus 100. In this example, if a user's residual limb is placed within the opening and is pushing against the compression bandage in a direction that towards the exit portion 208, then the released compression bandage will envelop the user's limb once the release mechanism 106 is activated.

In one embodiment, as illustrated in FIGS. 1 and 2, the release mechanism 106 is comprised of a slideably movable pin that travels through the length of the apparatus 100 in a direction. In one embodiment, the slideably movable pin may move in the same direction as a user's residual limb as it (the limb) pushes against the compression bandage. In another embodiment, the slideably movable pin may move in the opposite direction as a user's residual limb as it (the limb) pushes against the compression bandage. Once sufficient force is applied, and the pin 106 is activated, the compression bandage is released, which causes the compression bandage to envelop the limb that is pushing against the compression bandage.

The adjustment mechanism 108 permits a user to change the diameter or the size of the aperture/opening 102. In one embodiment, the adjustment mechanism 108 is comprised of a ratcheting system with interlocking teeth and a handle, wherein the interlocking teeth click or lock into place when a user manipulates the handle. The specific operation of the ratcheting system would be readily understood by a person of ordinary skill in the art. Moreover, any mechanism used to change the diameter/size of the aperture may be used, as would be understood by a person of ordinary skill in the art, without departing from the scope of the invention.

The apparatus 100 may also include an assistance mechanism 104 that helps a user manipulate the apparatus 100 and makes it easier to apply a compression bandage as described herein. In one embodiment, the apparatus 100 includes a handle 104. In one embodiment, only a singular handle or assistance mechanism 104 may be disposed on the inventive apparatus. However, in other embodiments, additional assistance mechanisms 104 may be provided. The assistance mechanism 104 permits a user to pull the apparatus closer to the user's body, while, at the same time, permitting a residual limb to travel through the opening in the direction that is away from the user's body. The assistance mechanism 104, therefore, makes it easier to use the inventive apparatus 100. The assistance mechanism 104 may include a variety of different shapes/designs, as would be readily understood by a person of ordinary skill in the art, including, handles wherein a user may slide his or her fingers within a handle opening, soft edge foam handles, handles with rubberized or texturized grip for a better grip, a bar type extension that a user may grasp within the palm of his or her hand, etc. In one embodiment, the assistance mechanism 104 may connect to another stationary platform or an object so that a user may apply a compression bandage around his or her residual limb by simply moving his or her limb through the opening without having to push the apparatus closer or away from his or her body.

In one embodiment, the assistance mechanism 104 may be comprised of an external support frame, which permits hands-free operation. In such an embodiment, the assistance mechanism 104 may include a stand or a mount that may attach to another object such that the user can simply push his or her residual limb through the opening 102 without having to otherwise hold the apparatus 100. Examples of stand/mounting systems include clamps or clips that may attach to a table, coupling grommets that may attach to a base unit or some other surface, etc. A person of ordinary skill in the art would readily understand the various specific mechanisms for mounting the apparatus 100 on a base/stand and/or other surfaces for stable operation. Use of any such system is contemplated herein and such usage would not depart from the scope of the invention.

The invention disclosed herein also includes a method for using the apparatus 100 described in the specification above. The method is comprised of the following steps: attaching a compression bandage to the attachment mechanism of the apparatus, moving a residual limb through the opening of the apparatus and pushing against the compression bandage that is extending across the bottom portion of the opening, releasing the compression bandage via a release mechanism once the residual limb is sufficiently through the inner opening, thereby causing the compression bandage to thoroughly envelop the residual limb.

Although the specification above makes references to using the apparatus with residual limbs (i.e. limbs that have been partially amputated), the system and methods described herein may be used with limbs that have undergone a variety of different types of injuries, including burns, swelling, diabetic ulcers, etc. The invention as described herein is not limited in scope for use with any particular injury type.

Additional Considerations

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the similar also includes the plural unless it is obvious that it is meant otherwise.

Upon reading this disclosure, those of skill in the art will appreciate still additional alternative structural and functional designs for a system and a process for creating an interactive message through the disclosed principles herein. Thus, while particular embodiments and applications have been illustrated and described, it is to be understood that the disclosed embodiments are not limited to the precise construction and components disclosed herein. Various apparent modifications, changes and variations may be made in the arrangement, operation and details of the method and apparatus disclosed herein without departing from the spirit and scope defined in the appended claims.

What is claimed is:

1. An apparatus for applying a compressive bandage on a residual limb that has been amputated, the apparatus comprising:
    a housing having an interior portion, an exterior portion, an entrance portion, and an exit portion, the interior portion defining an opening that is accessible from the entrance portion and the exit portion, the opening being large enough to accommodate a residual limb;
    an attachment mechanism for attaching a compressive bandage to the housing, the attachment mechanism enabling an attached compressive bandage to extend across the interior portion of the housing; and
    a release mechanism for releasing the attached compressive bandage from the attachment mechanism, the release mechanism configured to release the attached compressive bandage once the compressive bandage has sufficiently enveloped a residual limb that may be travelling through the opening defined by the interior portion.

2. The apparatus of claim 1, further comprising an adjustment mechanism for expanding and/or contracting the diameter of the opening, wherein the adjustment mechanism comprises a ratcheting system configured to be manipulated with a handle.

3. The apparatus of claim 2, wherein the adjustment mechanism expands and/or contracts the diameter of the entrance portion.

4. The apparatus of claim 2, wherein the adjustment mechanism expands and/or contracts the diameter of the exit portion.

5. The apparatus of claim 1, wherein the interior portion is tapered such that the diameter of the entrance portion is greater than the diameter of the exit portion.

6. The apparatus of claim 1, wherein the interior portion is tapered such that the diameter of the exit portion is greater than the diameter of the entrance portion.

7. The apparatus of claim 1, further comprising an assistance mechanism to assist a user in passing a residual limb through the opening.

8. The apparatus of claim 7, wherein the assistance mechanism is comprised of a handle that may be pulled and/or pushed to help a user pass a residual limb through the opening.

9. The apparatus of claim 7, wherein the assistance mechanism is disposed on the exterior portion of the apparatus.

10. The apparatus of claim 1, wherein the compression bandage serves as a transition layer between a residual limb and a prosthetic device.

* * * * *